US008828028B2

(12) United States Patent
Jacobsen et al.

(10) Patent No.: US 8,828,028 B2
(45) Date of Patent: Sep. 9, 2014

(54) SUTURE DEVICE AND METHOD FOR CLOSING A PLANAR OPENING

(75) Inventors: Stephen C. Jacobsen, Salt Lake City, UT (US); Fraser M. Smith, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 647 days.

(21) Appl. No.: 12/938,672

(22) Filed: Nov. 3, 2010

(65) Prior Publication Data
US 2011/0270277 A1 Nov. 3, 2011

Related U.S. Application Data

(60) Provisional application No. 61/257,746, filed on Nov. 3, 2009.

(51) Int. Cl.
*A61B 17/04* (2006.01)
*A61B 1/00* (2006.01)
*A61B 1/313* (2006.01)
*A61B 1/005* (2006.01)
*A61B 17/00* (2006.01)
*A61B 17/06* (2006.01)
*A61B 17/068* (2006.01)
*A61B 17/064* (2006.01)

(52) U.S. Cl.
CPC .......... *A61B 1/3137* (2013.01); *A61B 17/0469* (2013.01); *A61B 1/00154* (2013.01); *A61B 2017/00575* (2013.01); *A61B 2017/00663* (2013.01); *A61B 2017/06095* (2013.01); *A61B 2017/00296* (2013.01); *A61B 2017/00867* (2013.01); *A61B 2017/00668* (2013.01); *A61B 2017/00623* (2013.01); *A61B 2017/003* (2013.01); *A61B 17/068* (2013.01); *A61B 2017/0641* (2013.01); *A61B 1/0058* (2013.01)
USPC .......................................... 606/144; 600/109

(58) Field of Classification Search
CPC .......... A61B 1/05; A61B 1/051; A61B 1/053; A61B 17/06166; A61B 17/0618; A61B 17/06185; A61B 17/0619; A61B 17/06171; A61B 17/06176; A61B 17/06052
USPC ................................... 606/144; 600/109–112
See application file for complete search history.

(56) References Cited

U.S. PATENT DOCUMENTS

| 3,817,635 A | 6/1974 | Kawahar |
| 3,856,000 A | 12/1974 | Chikama |

(Continued)

FOREIGN PATENT DOCUMENTS

| CN | 1481753 | 3/2004 |
| DE | 197 42 973 | 4/1998 |

(Continued)

OTHER PUBLICATIONS

Gaoping et al.; Research on the Measurement of Grin Lens Focused Spot Diameter and Resolution; Applied Optics; 1995; vol. 16, No. 6.

(Continued)

*Primary Examiner* — Julian W Woo
*Assistant Examiner* — Shaun L David
(74) *Attorney, Agent, or Firm* — Thorpe North & Western LLP

(57) ABSTRACT

A micro-camera guided suturing device is disclosed comprising an elongate suture body having at least one lumen disposed therein and an imaging structure disposed within the at least one lumen of the suture. The imaging structure comprises a SSID optically coupled to a lens system. In one aspect, the suturing device further comprises a conductive element detachably coupled to the suture. In yet another aspect, the suture body comprises a shape memory material.

19 Claims, 12 Drawing Sheets

(56) References Cited

U.S. PATENT DOCUMENTS

| | | |
|---|---|---|
| 3,886,933 A | 6/1975 | Mori et al. |
| 3,918,438 A | 11/1975 | Hayamizu et al. |
| 3,971,065 A | 7/1976 | Bayer |
| 4,277,168 A | 7/1981 | Oku |
| 4,283,115 A | 8/1981 | Fraissl |
| 4,349,456 A | 9/1982 | Sowman |
| 4,360,275 A | 11/1982 | Louderback |
| 4,403,985 A | 9/1983 | Boretos |
| 4,475,902 A | 10/1984 | Schubert |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |
| 4,585,349 A | 4/1986 | Gross et al. |
| 4,588,294 A | 5/1986 | Siegmund |
| 4,589,404 A | 5/1986 | Barath et al. |
| 4,593,313 A | 6/1986 | Nagasaki et al. |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,626,079 A | 12/1986 | Nakamura et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takhashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,022,972 A | 6/1991 | David et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,369 A | 6/1992 | Srivastava |
| 5,126,639 A | 6/1992 | Srivastava |
| 5,130,804 A | 7/1992 | Tamura et al. |
| 5,165,063 A | 11/1992 | Strater et al. |
| 5,166,656 A | 11/1992 | Badehi et al. |
| 5,182,672 A | 1/1993 | Mukai et al. |
| 5,188,093 A | 2/1993 | Lafferty et al. |
| 5,190,523 A | 3/1993 | Lindmayer |
| 5,191,203 A | 3/1993 | McKinley |
| 5,198,894 A | 3/1993 | Hicks |
| 5,209,219 A | 5/1993 | Hollobaugh |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,408,999 A | 4/1995 | Singh et al. |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljie et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna |
| 5,547,906 A | 8/1996 | Badehi |
| 5,594,497 A | 1/1997 | Ahern |
| 5,603,687 A | 2/1997 | Hori et al. |
| 5,607,435 A * | 3/1997 | Sachdeva et al. ............ 606/139 |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,827,531 A | 10/1998 | Morrison et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |

(56) References Cited

U.S. PATENT DOCUMENTS

| | | |
|---|---|---|
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,139,819 A | 10/2000 | Unger et al. |
| 6,142,930 A | 11/2000 | Ito et al. |
| 6,161,035 A | 12/2000 | Furusawa |
| 6,184,923 B1 | 2/2001 | Miyazaki |
| 6,193,908 B1 | 2/2001 | Hampden-Smith et al. |
| 6,211,955 B1 | 4/2001 | Basiji et al. |
| 6,224,969 B1 | 5/2001 | Steenbergen et al. |
| 6,261,226 B1 | 7/2001 | McKenna et al. |
| 6,262,855 B1 | 7/2001 | Greisz |
| 6,271,206 B1 | 8/2001 | Pillai et al. |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsue |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikawa |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Swanson et al. |
| 6,525,866 B1 | 2/2003 | Lin et al. |
| 6,533,722 B2 | 3/2003 | Nakashima |
| 6,537,205 B1 | 3/2003 | Smith |
| 6,551,302 B1 | 4/2003 | Rosinko et al. |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hirata et al. |
| 6,585,717 B1 | 7/2003 | Wittenberg et al. |
| 6,595,913 B2 | 7/2003 | Takahashi |
| 6,618,614 B1 | 9/2003 | Chance et al. |
| 6,622,367 B1 | 9/2003 | Tu et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogenkijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speirer |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 * | 11/2010 | Nakao .................... 606/144 |
| 7,901,870 B1 | 3/2011 | Wach |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 | 3/2002 | Schulze et al. |
| 2002/0039594 A1 | 4/2002 | Unger |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Shuhei |
| 2002/0166949 A1 | 11/2002 | Shuhei et al. |
| 2002/0168776 A1 | 11/2002 | Cizdziel et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 | 6/2003 | Webler et al. |
| 2003/0197812 A1 | 10/2003 | Hirata et al. |
| 2003/0199761 A1 | 10/2003 | Yock |
| 2003/0202127 A1 | 10/2003 | Hirata et al. |
| 2003/0208211 A1 * | 11/2003 | Kortenbach ................. 606/151 |
| 2003/0220574 A1 | 11/2003 | Markus et al. |
| 2003/0222325 A1 | 12/2003 | Jacobsen et al. |

(56) References Cited

U.S. PATENT DOCUMENTS

| | | |
|---|---|---|
| 2004/0006274 A1 | 1/2004 | Giller et al. |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097804 A1 | 5/2004 | Lior |
| 2004/0111031 A1 | 6/2004 | Alfano et al. |
| 2004/0115955 A1 | 6/2004 | Motoyama et al. |
| 2004/0165858 A1 | 8/2004 | Curatolo |
| 2004/0181148 A1 | 9/2004 | Uchiyama et al. |
| 2004/0222031 A1 | 11/2004 | Szalony et al. |
| 2004/0225222 A1 | 11/2004 | Zeng et al. |
| 2004/0257566 A1 | 12/2004 | Chism |
| 2004/0260148 A1 | 12/2004 | Schnitzer |
| 2005/0054902 A1 | 3/2005 | Konno |
| 2005/0065504 A1 | 3/2005 | Melsky et al. |
| 2005/0084229 A1 | 4/2005 | Babbitt et al. |
| 2005/0088576 A1 | 4/2005 | Hirata et al. |
| 2005/0099824 A1 | 5/2005 | Dowling et al. |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0171521 A1 | 8/2005 | Brucker et al. |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0226636 A1 | 10/2005 | Hiramatsu et al. |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | Connor |
| 2006/0079835 A1 | 4/2006 | Frassica |
| 2006/0106283 A1 | 5/2006 | Wallace et al. |
| 2006/0135921 A1 | 6/2006 | Wiercinski et al. |
| 2006/0142700 A1 | 6/2006 | Sobelman et al. |
| 2006/0146172 A1 | 7/2006 | Jacobsen et al. |
| 2006/0161048 A1 | 7/2006 | Squicciarini |
| 2006/0181774 A1 | 8/2006 | Ojima et al. |
| 2006/0252994 A1 | 11/2006 | Ratnakar |
| 2006/0253088 A1 | 11/2006 | Chow et al. |
| 2007/0010709 A1 | 1/2007 | Reinschke |
| 2007/0032796 A1 | 2/2007 | Chin-Chen et al. |
| 2007/0073321 A1 | 3/2007 | Mikkaichi et al. |
| 2007/0083232 A1 | 4/2007 | Lee |
| 2007/0088276 A1 | 4/2007 | Stubbs et al. |
| 2007/0135803 A1 | 6/2007 | Belson |
| 2007/0146887 A1 | 6/2007 | Ikeda et al. |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0058601 A1 | 3/2008 | Fujimori |
| 2008/0071141 A1 | 3/2008 | Gattani et al. |
| 2008/0094326 A1 | 4/2008 | Yamaki et al. |
| 2008/0114309 A1 | 5/2008 | Zuckerman |
| 2008/0160257 A1 | 7/2008 | Takada et al. |
| 2008/0177141 A1 | 7/2008 | Wu et al. |
| 2008/0183080 A1 | 7/2008 | Abraham |
| 2008/0188767 A1 | 8/2008 | Oaki et al. |
| 2008/0227893 A1 | 9/2008 | Tamori et al. |
| 2008/0267562 A1 | 10/2008 | Wang et al. |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1 | 3/2009 | Ichimura et al. |
| 2009/0119808 A1 | 5/2009 | Giakos |
| 2009/0137928 A1 | 5/2009 | Quick et al. |
| 2009/0143645 A1 | 6/2009 | Matthes |
| 2009/0155371 A1 | 6/2009 | Sojka et al. |
| 2009/0156899 A1 | 6/2009 | Konishi |
| 2009/0180197 A1 | 7/2009 | Jacobsen et al. |
| 2009/0213894 A1 | 8/2009 | Grapov et al. |
| 2009/0234325 A1 | 9/2009 | Rozenberg et al. |
| 2009/0267270 A1 | 10/2009 | Murakami et al. |
| 2009/0287048 A1 | 11/2009 | Jacobson et al. |
| 2010/0085567 A1 | 4/2010 | Dottery et al. |
| 2010/0106134 A1 | 4/2010 | Jolly et al. |
| 2010/0134872 A1 | 6/2010 | Johnson et al. |
| 2010/0171821 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | 63-155115 | 6/1988 |
| JP | H05-039501 | 2/1993 |
| JP | 5-049602 | 3/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004-086553 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-20080027935 | 3/2008 |
| WO | WO98/38907 | 9/1998 |
| WO | WO99/40624 | 8/1999 |
| WO | WO00/54033 | 9/2000 |
| WO | WO 03/081831 | 10/2003 |
| WO | WO2006/060777 | 6/2006 |
| WO | WO 2007/138889 | 12/2007 |

OTHER PUBLICATIONS

PCT Application PCT/US2010/051188; filed Oct. 1, 2010; Stephen C. Jacobsen; International Search Report mailed Jul. 13, 2011.

Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.

Xuting Technologies Co., Ltd.; http://www.xutingby.com/en/products/glinfo.htm; as accessed May 1, 2008; 5 pages.

Frequency; Wikipedia, The Free Encyclopedia; http://en.wikipedia.org/wiki/Frequency; as accessed May 9, 2008; 4 pages.

Introduction to Gradient Index Optics; http://grintech.de/e_main_grin.htm; as accessed May 1, 2008; 7 pages.

Gradient Index (GRIN) Lenses; Grin Tech; 2 pages; The Applicant believes the year of publication of this article is prior to the effective US filing date of this patent application.

Shape Memory Polymers—Biodegradable Sutures; http://www.azom.com/details.asp?ArticleID=1542; as accessed Nov. 6, 2007; 4 pages.

Surgical Needles for Use With Sutures; Wikipedia, The Free Encyclopedia; as accessed Nov. 6, 2007; 6 pages.

(56) References Cited

OTHER PUBLICATIONS

Harder et al; Against the Migraine; Science News Online; http://www.sciencenews.org/articles/20050219/bob8.asp; Feb. 19, 2005; 11 pages.

U.S. Appl. No. 12/152,730, filed May 16, 2008; Stephen C. Jacobson; office action issued Sep. 16, 2011.

PCT Application PCT/US2010/051200; filed Oct. 1, 2010; Stephen C. Jacobsen; ISR mailed Jun. 3, 2011.

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

U.S. Appl. No. 12/487,481, filed Jun. 18, 2009; Stephen C. Jacobsen; office action dated Oct. 12, 2012.

U.S. Appl. No. 12/512,188, filed Jul. 30, 2009; Stephen C. Jacobsen; office action dated Nov. 19, 2012.

Obreja et al.; "Poly (vinyl-alcohol) Films for Microphotonics"; 2004, IEEE, pp. 1-4.

Boppart, S.A. et al., "Forward-imaging instruments for optical coherence tomography." Optics Letters, Nov. 1, 1997, vol. 22, No. 21, pp. 1618-1620.

Boppart, S.A. et al., "Optical imaging technology in minimally invasive surgery," Surg. Endosc., 1999, vol. 13, pp. 718-722.

Fujimoto, Jg et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

http://news.thomasnet.com/fullstory/23462, "Near-IR Camera Utilizes CCD Array With Phosphor Coating"; Jun. 11, 2003; 5 pages.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 11/810,702, filed Jun. 5, 2007.

Jacobsen, Stephen C., U.S. Appl. No. 12/008,486, filed Jan. 11, 2008.

Jacobsen, Stephen C., U.S. Appl. No. 12/079,741, filed Mar. 27, 2008.

Jacobsen, Stephen C., U.S. Appl. No. 12/152,730, filed May 16, 2008.

Jacobsen, Stephen C., U.S. Appl. No. 12/487,481, filed Jun. 18, 2009.

Jacobsen, Stephen C., U.S. Appl. No. 12/487,495, filed Jun. 18, 2009.

Jacobsen, Stephen C., U.S. Appl. No. 12/512,188, filed Jul. 30, 2009.

Jacobsen, Stephen C.; U.S. Appl. No. 12/611,776, filed Nov. 3, 2009.

Jacobsen, Stephen C.; U.S. Appl. No. 12/792,562, filed Jun. 2, 2010.

Jacobsen, Stephen C.; U.S. Appl. No. 12/896,731, filed Oct. 1, 2010.

Jacobsen, Stephen C.; U.S. Appl. No. 12/896,732, filed Oct. 1, 2010.

Jacobsen, Stephen C.; U.S. Appl. No. 12/896,737, filed Oct. 1, 2010.

Jacobsen, Stephen C.; U.S. Appl. No. 12/896,743, filed Oct. 1, 2010.

Jacobsen, Stephen C.; U.S. Appl. No. 12/946,442, filed Nov. 15, 2010.

Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.

Literature from GRIN Tech, "In vivo medical confocal imaging and optical coherence tomography," www.grintech.de, Revision Jun. 2001, pp. 1-3.

Microcam, Minast Project 5.04, Nov. 11, 1999, http://www.imt.unine.ch/ESPLAB/www/projects/Microcam/, pp. 1-16.

Nguyen, Clark, "Communications Applications of Microelectromechanical Systems," Proceedings, Sensors Expo, May 19-21, 1998, San Jose, CA. pp. 447-455.

Tearney, G.J. et al., "Scanning single-mode fiber optic catheter-endoscope for optical coherence tomography," Optics Letters, Apr. 1, 1996, vol. 21, No. 7, pp. 543-545.

Zeis, Michael et al., "Color Business Report," ISSN 1055-3339. Jul. 2002, p. 5.

\* cited by examiner

SUTURE DEVICE AND METHOD FOR CLOSING A PLANAR OPENING

PRIORITY CLAIM

This application claims priority to U.S. Provisional Application No. 61/257,746 filed on Nov. 3, 2009 which is incorporated herein by reference in its entirety.

BACKGROUND

Minimally invasive diagnostic medical procedures are used to assess the interior surfaces of an organ by inserting a tube into the body. The instruments utilized may have a rigid or flexible tube and provide an image for visual inspection and photography, but also enable taking biopsies and retrieval of foreign objects. Analysis of image data collected during the inspection and photography of the interior of the body cavity is a critical component of proper diagnosis of disease and other related conditions.

Percutaneous catheterization is a type of medical treatment that is generally less-invasive than directly accessing an internal body site for treatment, such as when using general surgery methods. In catheterization techniques, a long tubular catheter is introduced into the body through a puncture site. It is then passed to that site, usually through passageways such as the vascular tree. Treatment or diagnostic procedures may then be accomplished using the catheter by manipulation of the portion of the catheter remaining outside the body.

It is not uncommon to use percutaneous catheterization to introduce sutures into internal portions of the body in an effort to correct physiological defects, close unwanted openings, or conduct other medical procedures. Existing technology for accomplishing these tasks suffer from the inability to place a suture or conduct a medical procedure with a single tool capable of placing a suture and viewing placement of the suture from the perspective of the suture itself.

SUMMARY OF THE INVENTION

In light of the problems and deficiencies inherent in the prior art, the present invention seeks to overcome these by providing a micro-camera guided suturing device. In one embodiment, the device comprises a suture having at least one lumen disposed therein. An imaging structure is disposed within the at least one lumen of the suture. The imaging structure comprises a SSID optically coupled to a lens system. In one aspect, the microcamera guided suturing device further comprises a conductive element detachably coupled to the suture.

In yet another aspect, the suture comprises a shape memory material. In one embodiment of the present invention, the shape memory material comprises a shape memory alloy such as copper-zinc-aluminum-nickel, copper-aluminum-nickel, or nickel-titanium alloys. In another embodiment, the shape memory material comprises a shape memory polymer (e.g., a bioabsorbable polymer).

In another embodiment of the present invention, a distal end of the lens system is disposed near a distal end of the suture. In one aspect, the at least one lumen extends longitudinally through approximately the entire suture. In yet another aspect, the image plane of the imaging structure is approximately collinear with a distal end of the suture.

In accordance with an additional embodiment of the present invention, a microcamera guided suturing device is disclosed, comprising a suture comprising a shape memory material biased in a first position and configured to assume a second position when subjected to a predetermined temperature paradigm. The device further comprises a micro-camera comprising a SSID and a lens system optically coupled to the SSID. The micro-camera is detachably coupled to the suture. A distal end of the lens system is disposed near a distal end of the suture. In one aspect of the invention, the device further comprises a restraining device disposed about the suture maintaining the suture in a closed position.

In one embodiment of the present invention, a method of placing suture within a patient is disclosed comprising providing a suture disposed on a distal end of a catheter, wherein the suture is a shape memory material having at least one lumen disposed therein. Providing an imaging structure disposed within the at least one lumen of the suture, the imaging structuring comprising a SSID optically coupled to a lens system. The method further comprises advancing a distal end of the catheter into a portion of a patient. The method further comprises viewing a portion of the interior of the patient with the imaging structure and emplacing the suture within a portion of the patient.

In one aspect of the invention, a conductive element is detachably coupled to the suture. In this aspect, the method further comprises the step of conducting electrical energy to the suture through the conductive element. The method further comprises the step of withdrawing the imaging structure from the suture.

An additional embodiment of the present invention comprises a method of placing a suture within a patient comprising providing a suture disposed on a distal end of a catheter. The suture comprises a shape memory material and an imaging structure detachably coupled to the suture. The imaging structuring comprises a SSID optically coupled to a lens system. The method further comprises advancing a distal end of the catheter into a portion of a patient and viewing a portion of the interior of the patient with the imaging structure. The method further comprises emplacing the suture within a portion of the patient while viewing emplacement of the suture with the imaging structure.

In one aspect of the invention, the method further comprises detaching the imaging structure from the suture and withdrawing the catheter and imaging structure from the patient. In an additional aspect, the suture has a conductive element detachably coupled to the suture. In this aspect, the method further comprises the step of conducting electrical energy to the suture through the conductive element.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

DETAILED DESCRIPTION OF EXAMPLE EMBODIMENT(S)

Figure 1:
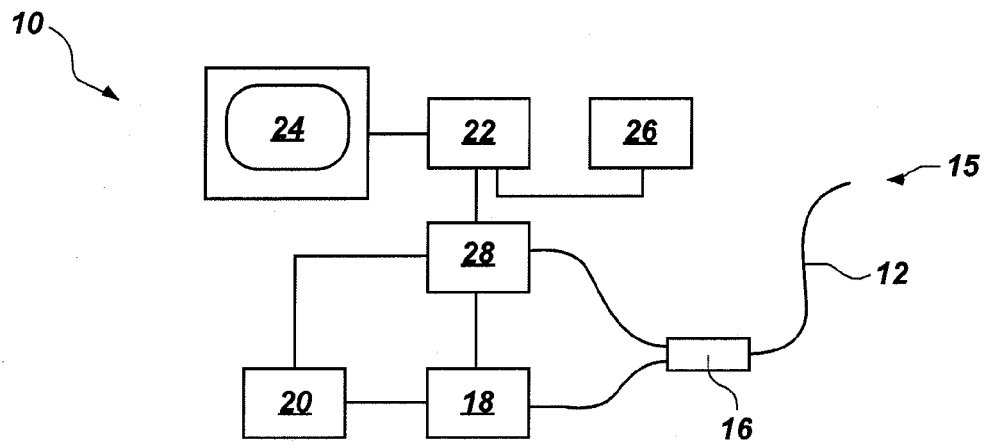
FIG. 1 is an exemplary view of a medical imaging system in accordance with an embodiment of the present invention.

Reference will now be made to, among other things, the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," "SSID chip," or "solid state imaging chip" in the exemplary embodiments generally comprises an imaging array or pixel array for gathering image data, and can further comprise conductive pads electrically coupled to the imaging array, which facilitates electrical communication therebetween. In one embodiment, the SSID can comprise a silicon or other semiconductor substrate (e.g., InGaAs) or amorphous silicon thin film transistors (TFT) having features typically manufactured therein. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens.

With these definitions in mind, reference will now be made to, among other things, the accompanying drawings, which illustrate, by way of example, embodiments of the invention.

Turning to the drawings, in which like reference numerals represent like or corresponding elements in the drawings, in one embodiment of the present invention, FIG. 1 illustrates a medical imaging system 10 is disclosed comprising a micro-catheter 12 having an imaging device disposed at a distal tip 15 of the micro-catheter 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical, including conductive wires through the micro-catheter 12. A light source may also be provided at the distal end of the micro-catheter 12. In one aspect, the system further includes a fitting 16 enabling an imaging fluid, such as a clear saline solution, to be dispensed to the distal tip portion of the micro-catheter 12 from a reservoir 18 through an elongated tubular member removably attached to the micro-catheter 12 or through a lumen of the microcatheter to displace body fluids as needed to provide a clearer image. Fluids may be pumped to the distal end of the micro-catheter for other reasons described herein. A pump 20 is provided, and is manually actuated by a medical practitioner performing a medical imaging procedure, or can be automated and electronically controlled so as to dispense fluid on demand according to control signals from the practitioner, sensors, or according to software commands.

Figure 2:
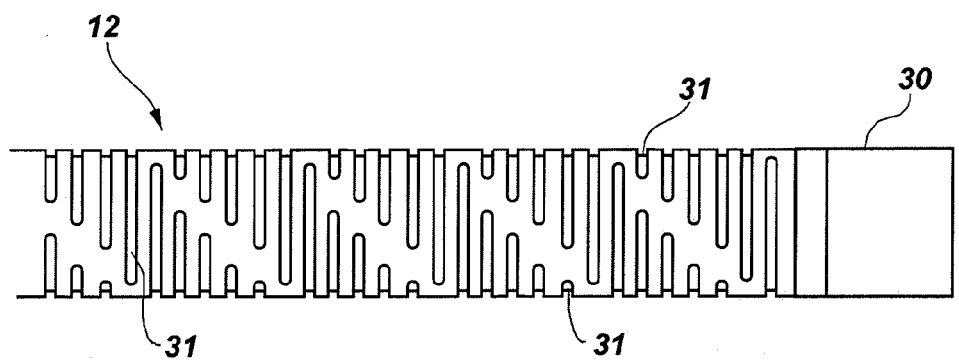
FIG. 2 is a side view of a micro-catheter in accordance with one embodiment of the present invention.
Figure 3:
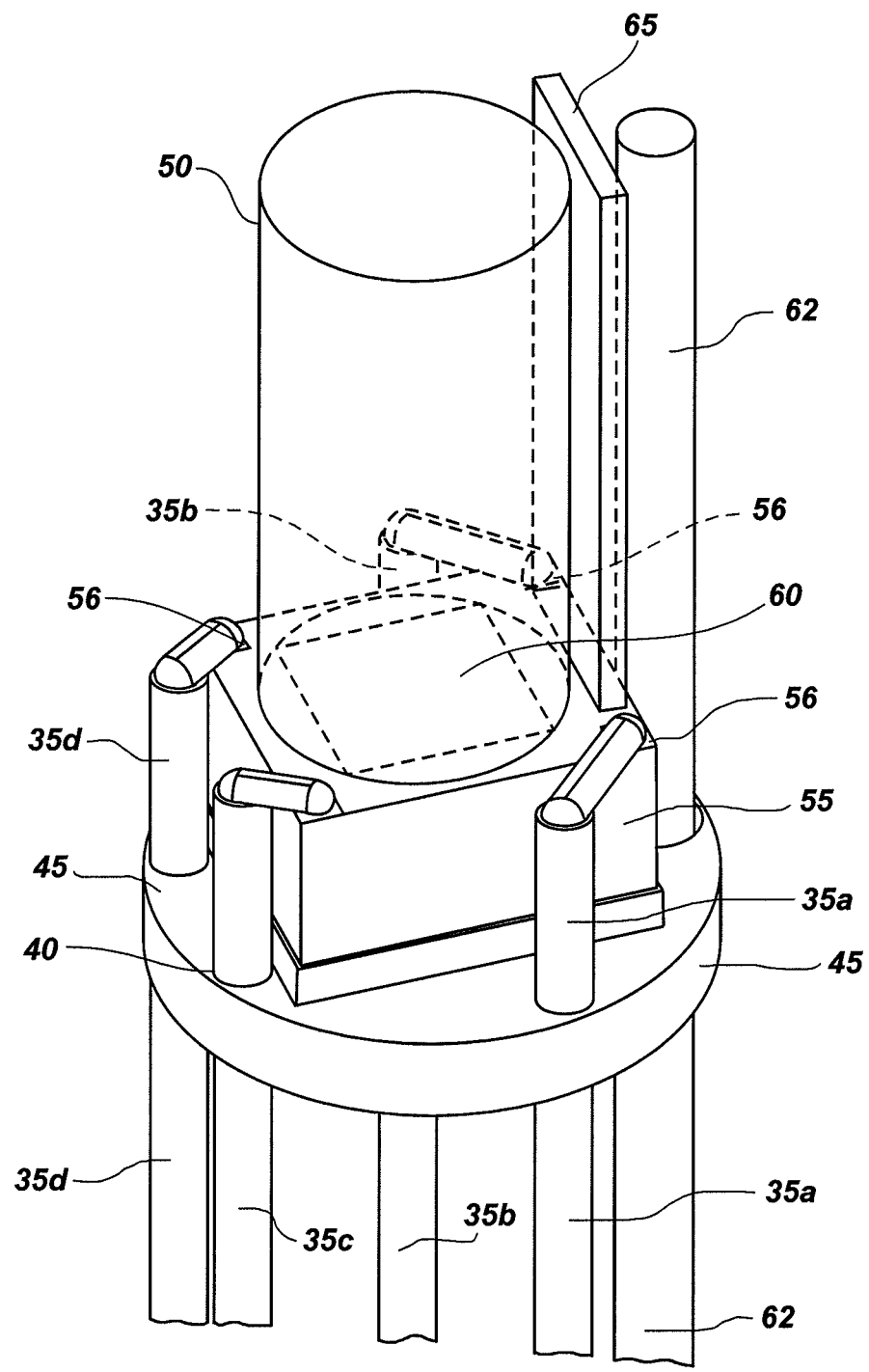
FIG. 3 is a perspective view of an imaging structure according to one embodiment of the present invention.

With reference now to FIGS. 2 and 3, according to one embodiment of the present invention, an imaging device 30 is disposed on a distal end of a micro-catheter 12. Micromachined cuts 13 are disposed non parallel to a longitudinal direction of the micro-catheter 12 to enable a user, such as a medical practitioner, to guide and steer the distal end of the micro-catheter 12 within a cavity of a patient. In one aspect of the present invention, the micro-catheter may incorporate structure and principles of operation from a catheter disclosed in U.S. Pat. No. 6,014,919 to Jacobsen et al., which is incorporated herein by reference.

In one aspect of the invention, imaging device 30 comprises at least two conductive wires 35a, 35b for conducting electronic image data to the data processor 22 and for securing an imaging structure 36 between the at least two conductive wires 35a, 35b. As illustrated in FIG. 3 however, a plurality of conductive wires 35a, 35b, 35c, 35d may be utilized.

The at least two conductive wires 35a, 35b are oriented along a longitudinal axis of the imaging structure 36 and are disposed within alignment apertures 40 of a planar support member 45. The planar support member 45 comprises at least two alignment apertures 40 disposed on opposing sides of the planar support member 45. The alignment apertures 40 are configured to receive and align the at least two conductive wires 35a, 35b along the longitudinal axis of the imaging structure 36. The imaging structure 36 is at least partially secured between the at least two conductive wires 35a, 35b and is disposed adjacent a top surface of the planar support member 45. In one aspect of the invention, the imaging structure 36 comprises a GRIN lens 50 optically coupled to a SSID 55 and disposed adjacent the SSID 55. The imaging structure further comprises an imaging array 60 disposed on a top surface of the SSID 55. In one embodiment, the GRIN lens 50 is positioned directly on top of the imaging array 60 of the SSID 55. The at least two conductive wires 35a, 35b are operatively coupled to the imaging structure 36 and are configured to align the imaging structure 36 there between. In one aspect, the conductive wires 35a, 35b are bonded to the imaging structure 36 at contact points 56 disposed on the periphery of a top surface of the SSID 55. In yet another embodiment, the conductive wires 35a, 35b are bonded to a side surface of the SSID 55.

In one embodiment, the alignment apertures 40 are oriented perpendicular to the top surface of the planar support member 45. However, the alignment apertures may also be disposed in any orientation which is not non-parallel to the planar support member 45 as required to optimally align the imaging structure 36 as desired. In one embodiment, the imaging structure is mounted and aligned such that the image plane of the imaging structure 36 is non parallel to a longitudinal axis of the micro-catheter 12. In one aspect of the invention, a light source (e.g., a fiber optic member, LED, etc.) 62 is disposed within an aperture of the planar support member 40 to provide light for imaging. In yet another aspect of the present invention, the imaging structure 30 may incorporate structure and principles of operation from an imaging device disclosed in U.S. Pat. No. 7,166,537 to Jacobsen et al., which is incorporated herein by reference.

Figure 4:
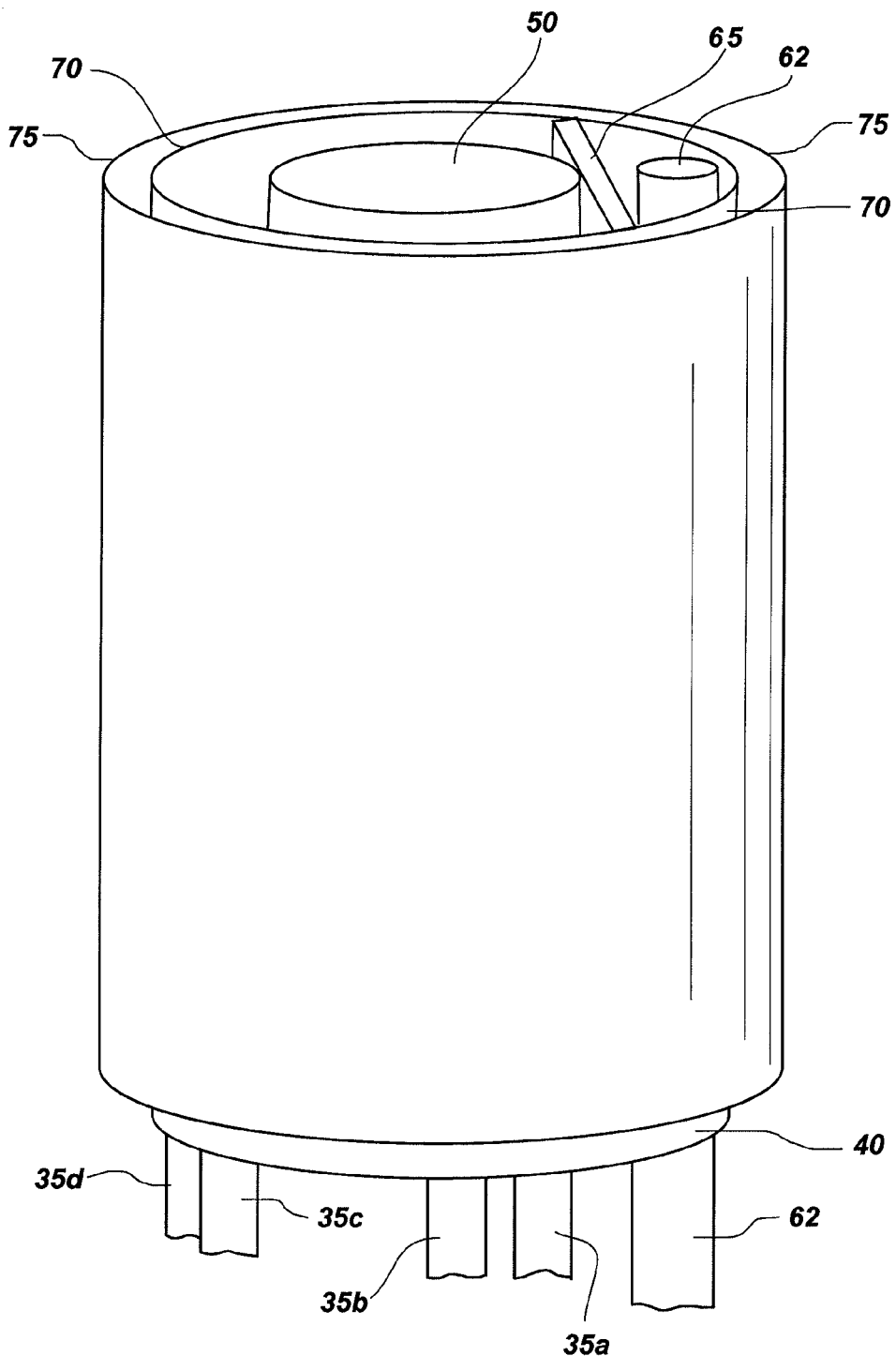
FIG. 4 is a perspective view of an imaging structure according to one embodiment of the present invention.
Figure 5:
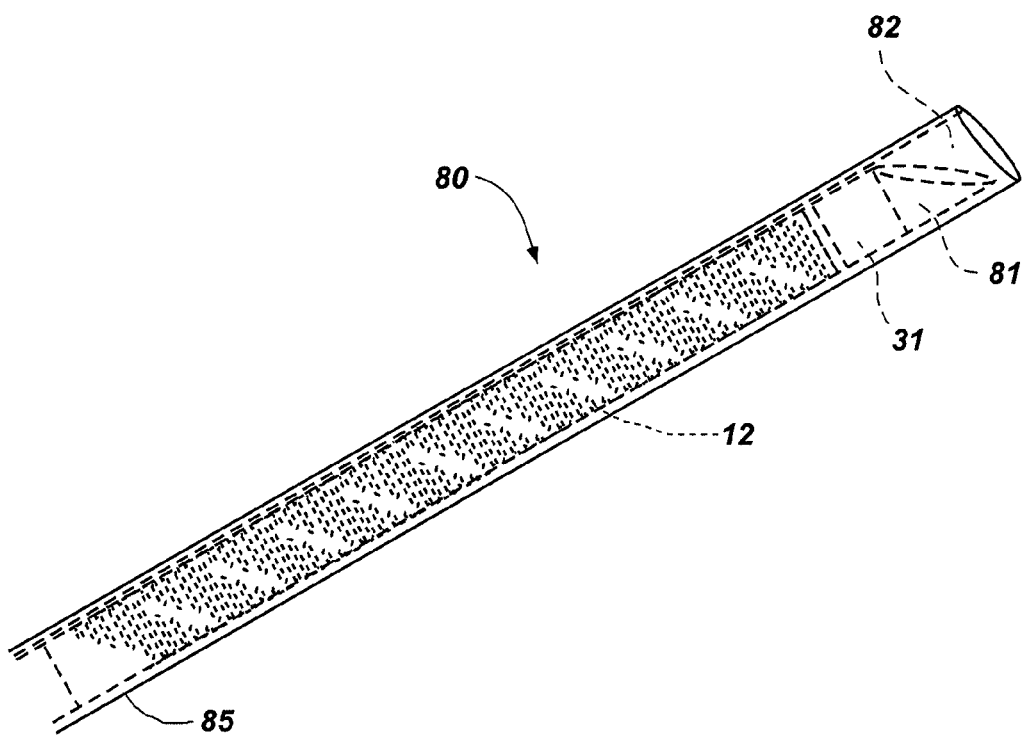
FIG. 5 is a side-view of a micro-camera guided suturing device according to one embodiment of the present invention.
Figure 6:
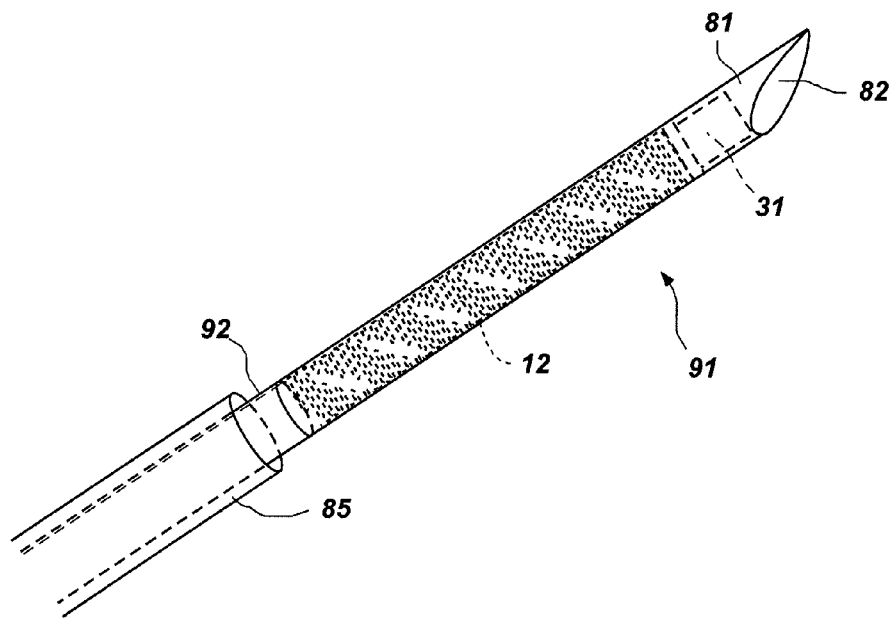
FIG. 6 is a side-view of a micro-camera guided suturing device according to one embodiment of the present invention.
Figure 7:
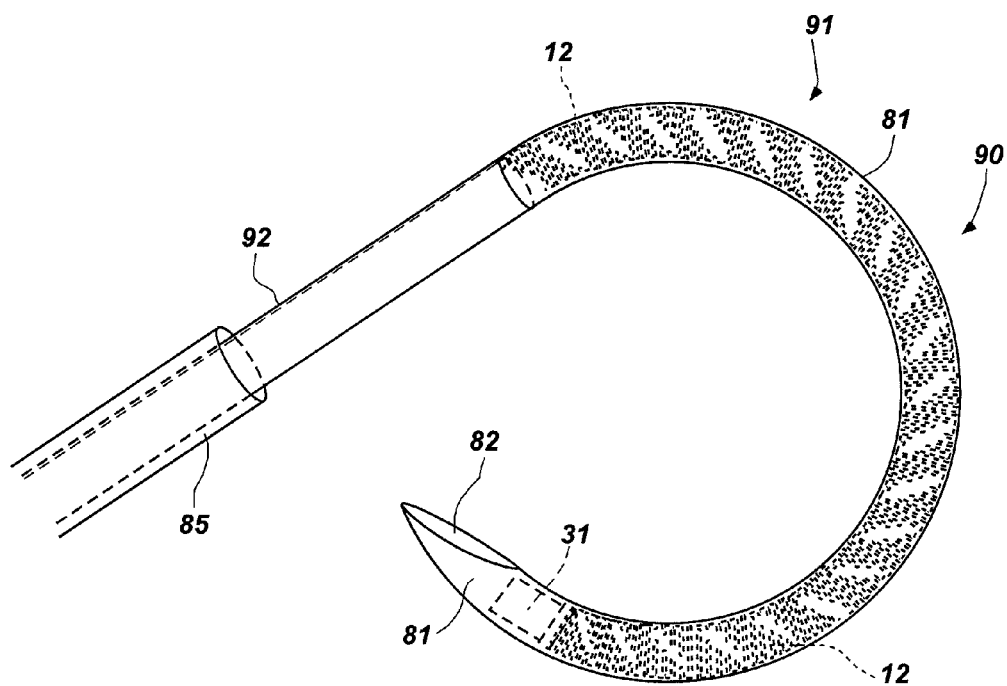
FIG. 7 is a side-view of a micro-camera guided suturing device according to one embodiment of the present invention.
Figure 8:
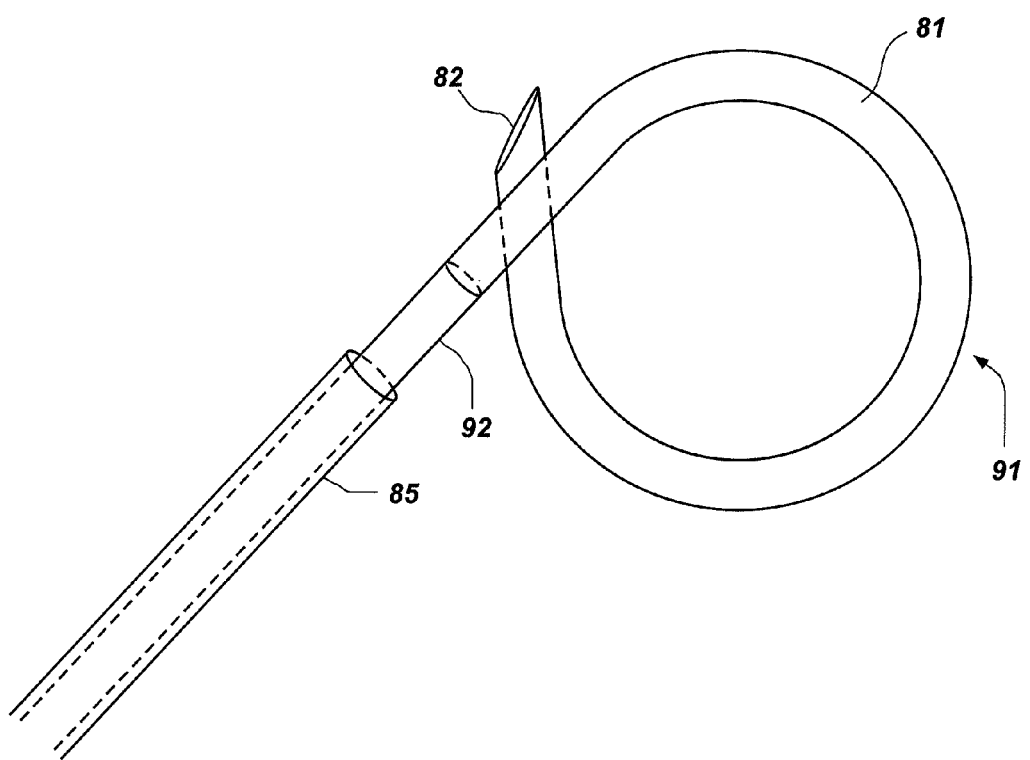
FIG. 8 is a side-view of the micro-camera guided suturing device of FIG. 7 according to one embodiment of the present invention with the micro-camera portion of the device removed.
Figure 9:
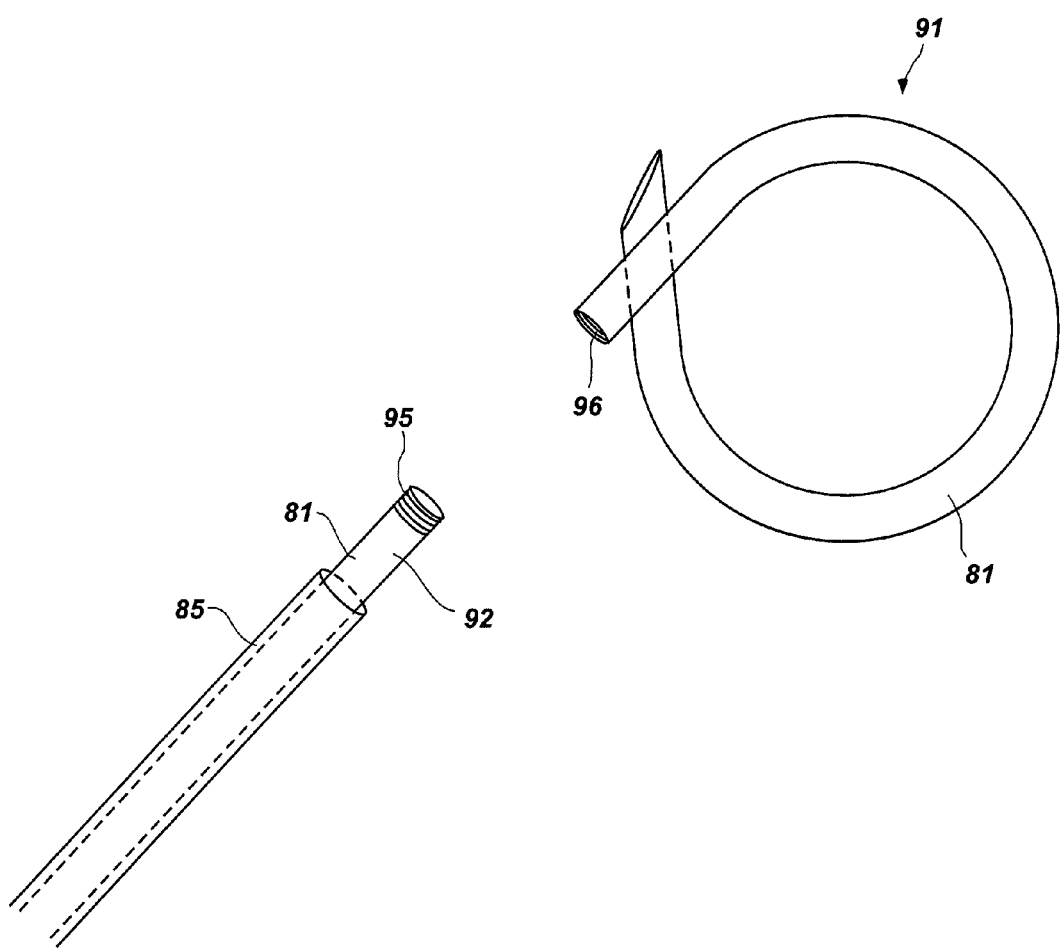
FIG. 9 is a side-view of the micro-camera guided suturing device according to one embodiment of the present invention.

Referring now to FIGS. 3 and 4, in yet another embodiment of the present invention, the imaging device 30 further comprises a lens support member 65. In one aspect, the lens support member 65 is bonded to a top surface of the SSID 55. In another aspect, the lens support member 65 is bonded to a side surface of the SSID 55. In yet another aspect, the lens support member 65 is bonded to a top surface of the planar support member 40. In any event, the lens support member 65 is oriented adjacent a side surface of the GRIN lens 50 to minimize movement of the GRIN lens 50 during operation and to ensure proper alignment of the GRIN lens 50 on the imaging array 60 during operation and/or construction of the device. In one aspect of the invention, a first sleeve member 70 is disposed about the imaging structure 36. An adhesive is disposed within the first sleeve member 70 securing the components of the imaging structure 36 in place as well as securing the first sleeve member 70 to the imaging structure 36. In an additional embodiment, a second sleeve member 75 is disposed about the first sleeve member 70 and secured with an adhesive. In one aspect of the invention, the second sleeve member 75 comprises an opaque material to eliminate secondary light from impacting image quality.

Referring now to FIGS. 5-8, according to one embodiment of the present invention, a micro-camera guided suturing device 80 is disclosed having a suture 81 comprising a shape memory material with at least one lumen 82 disposed therein. The suturing device 80 further comprises an imaging structure 31 disposed within the at least one lumen 82 of the suture 81, wherein the imaging structure 31 comprises a SSID 55 optically coupled to a lens system 50. In one aspect, the micro-camera guided suturing device 80 further comprises an outer catheter 85 which houses the suturing device 80 during advancement of the suturing device through portions of the body (e.g., the vascular tree). Due to the very small nature of the imaging structure 31 (e.g., less than 0.5 mm), it may advantageously be placed within the lumen 82 of the suture 81. In one aspect, the lumen 82 has an internal diameter of approximately 0.5 mm. However, it is understood that the inner diameter of the lumen 82 of the suture 81 may be smaller to accommodate a smaller imaging structure 81 as suits a particular application. It is important to note that the suture 81 need not be made of a shape memory material as described herein to satisfy each and every application of the certain aspects of the present invention. For example, in one aspect of the invention, the suture 81 comprises a semi-rigid or rigid material which cannot undergo a significant change in shape without suffering plastic deformation.

In one aspect of the invention, a conductive element (not shown) is detachably coupled to the suture 81. The conductive element (not shown) acts to transfer energy to the suture to effectuate the shape change of the suture 81 due to the intrinsic properties of the shape memory material. In accordance with one embodiment of the invention, the shape memory material of the suture 81 comprises a shape memory alloy. Examples of shape memory alloy contemplated for use herein include, without limitation, copper-zinc-aluminum-nickel, copper-aluminum-nickel, or nickel-titanium alloys or any other suitable alloy which changes shape when subjected to varying predetermined temperatures. In yet another embodiment of the present invention, the shape memory material of the suture 81 comprises a shape memory polymer such as a oligo(e-caprolactone)diol and crystallisable oligo (p-dioxamone)diol, or any other suitable polymer which assumes a predetermined shape when subject to a predetermined temperature. In one aspect, the shape memory material is bio-absorbable in that it comprises materials which are broken down by the body over time.

In one aspect of the invention, at least one lumen 82 extends longitudinally through approximately the entire suture 81. However, in another embodiment, the at least one lumen 82 may extend longitudinally through only a portion of the suture 81 as may be desirable for a particular application. In an additional aspect, an image plane of the imaging structure 31 is approximately collinear with a distal end of the suture 81. Additionally, the distal end of the lens system is disposed near a distal end of the suture to facilitate viewing of the body during emplacement of the suture. In this manner, a medical practitioner may view the area of the body where the suture 81 is being placed and may also view the body during emplacement of the suture to verify proper placement of the suture. Advantageously, improper placement of sutures within the body may be reduced thereby minimizing unnecessary trauma to a patient.

In one aspect, a medial portion 91 of the suture 81 is detachably coupled to the end portion of the suture 92. The medial portion 91 of the suture 81 may be coupled to the remaining portion of the suture by a threaded male member 95 and corresponding threaded female member 96 configured to receive the male member 95. However, it is understood that any system or device capable of detachably connecting the medial portion 91 of the suture 81 with the remaining portion of the suture 81 is contemplated for use herewith. In this manner, the medial portion 91 of the suture 81 may be emplaced within the patient and the remaining components of the suturing device 80 may be removed from the patient.

Figure 16A:
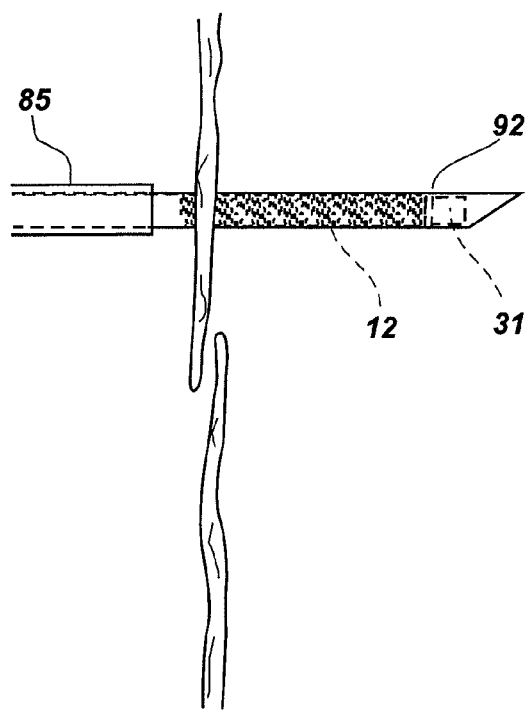
FIG. 16A is a side view of a suture device according to one embodiment of the present invention.
Figure 16B:
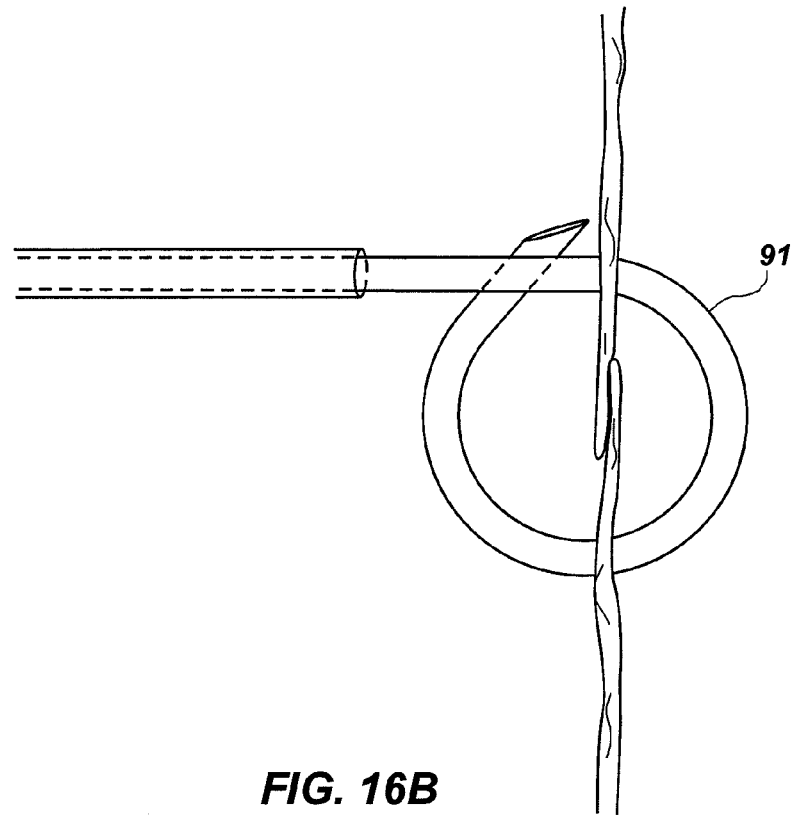
FIG. 16B is a side view of an emplaced suture according to one embodiment of the present invention.

With reference now to FIGS. 16A and 16B, according to one aspect of the invention, a medical practitioner may guide the suturing device 80 to a particular location within the body of a patient and emplace the suture 81 in a desired location. For example, in one embodiment, the suture 105 may comprise a shape memory alloy which assumes a particular shape when subjected to a predetermined temperature. In yet another embodiment, the suture 81 may comprise a malleable, deformable material (e.g., an aluminum alloy) which bends in response to forces exerted by the steering movements of the micro-catheter 12 in which the suture 81 is placed. In one aspect of the invention, a medical practitioner may guide the micro-catheter to a desired location within the patient. While in an at least substantially straight orientation, the distal end of the suture 81 may be placed through a portion of tissue near an area that requires suturing. Electrical current may be applied to the suture thereby deforming the suture 81 into a closed configuration (e.g., a loop shape). As the suture 81 deforms into a closed configuration, its distal end pierces a corresponding portion of tissue and closes the desired target area. Advantageously, a medical practitioner may view the target tissue being penetrated by the suture 81 in real time thereby ensuring proper placement of the suture 81. It is important to note that the suture 81 may be preformed in a variety of configurations and may be designed to assume a variety of different shapes depending on a particular application. For example, but without limitation, the suture 81 may be biased in a hook configuration (not shown) and configured to close more tightly into a loop configuration as shown on FIG. 16B. Alternatively, the suture 81 may be comprised of a non-shape memory material and be biased in a hook configuration in a rigid state or semi-rigid state as suits a particular application.

It is important to note that while reference is made herein to a single imaging device disposed within the suture, multiple imaging devices may be employed to emplace a suture into a patient. That is, a medical device employing embodiments of the present invention may comprise an imaging device disposed within a suture and may also comprise an imaging device at the distal end of the medical device so as to provide multiple views of the emplacement of the suture including an imaging device to provide a perspective view of suture emplacement as well as the imaging device within the suture to provide the "suture-view" of the emplacement.

In an additional embodiment, a suturing device 80 may comprise a plurality of sutures disposed on a distal end of the device 80 configured such that any one of the plurality or all of the plurality of sutures may be placed without the need for advancement of a device through the vasculature of a patient multiple times. That is, in some instances there may be a need to emplace numerous sutures within a patient. This embodiment allows a single device to be placed within the vasculature of the patient once while providing the medical practitioner with the ability to place multiple sutures. Moreover, while not shown in the accompanying figures, it is understood that additional tools may be used in connection with the suturing device to accomplish medical procedures including, but not limited to, cauterizers, forceps, clamps, laser diodes, etc. Additionally, the suturing device 80 may be used as a stand-alone device or may be used as one tool in connection with an endoscopic device capable of housing multiple tools. An exemplary endoscopic tool is illustrated in U.S. patent application Ser. No. 11/292,902 which is incorporated herein by reference.

With reference to FIGS. 3, 4, 10, and 11, according to one embodiment of the present invention, a micro-camera guided suturing device 100 comprising a suture 105 detachably coupled to a micro-catheter 12 is illustrated. The micro-catheter 12 comprises an imaging structure 31 having an SSID 55 optically coupled to a lens system 50. In one aspect, the micro-camera guided suturing device 100 further comprises an outer catheter 110 which houses the suturing device 100 during advancement of the suturing device through portions of the body. In one aspect of the invention, a distal end 101 of the micro-catheter 12 is shaped to approximate the distal end of a needle facilitating penetration into tissues of a patient. In one aspect, the suture 105 and micro-catheter 12 are each shaped to approximate a cylinder which has been halved down a longitudinal axis of the cylinder. In this manner, when the suture 105 and micro-catheter 12 are joined together they form a whole cylinder. To be clear, in one embodiment of the present invention the suture 105 and micro-catheter 12 each comprise a planar surface and an opposing half-circle surface such that when the two are joined together at their respective planar surfaces, the two form a single cylindrical body. Advantageously, the mating components of the suture 105 and micro-catheter 12 facilitate easier penetration into tissues of a patient thereby reducing unnecessary trauma to the tissue and the patient.

In one embodiment, the suture 105 may comprise a shape memory alloy which assumes a particular shape when subjected to a predetermined temperature. In yet another embodiment, the suture 105 may comprise a malleable, deformable material (e.g., an aluminum alloy) which bends in response to forces exerted by the steering movements of the micro-catheter 12 to which the suture 105 is attached.

In an additional embodiment, the suture 105 is detachably coupled to a side portion of the micro-catheter 12. In one aspect, the suture 105 is detachably coupled to a side portion 102 of the micro-catheter 12 by a temperature sensitive adhesive whereby when the interface between the suture 105 and the micro-catheter 12 is subjected to a certain temperature, the adhesive becomes unstable and no longer secures the suture 105 to the micro-catheter 12. The adhesive may be designed to react to the temperature within the patient or may be designed to react to heating through an electrical element disposed about the micro-catheter. While use of an adhesive has been specifically described, it is contemplated herein that use of any means capable of detachably coupling and facilitating detachment of the micro-catheter 12 from the suture 105 may be used as is suitable for a particular application.

With reference now to FIGS. 12-15, according to one embodiment of the present invention, a micro-camera guided suturing device 150 comprising a suture 160 detachably coupled to a micro-catheter 12 is illustrated. The micro-catheter 12 comprises an imaging structure 31 having an SSID 55 optically coupled to a lens system 50. In one aspect, the micro-camera guided suturing device 150 further comprises an outer catheter 165 which houses the suturing device 150 during advancement of the suturing device 150 through portions of the body. According to one aspect of the invention, the suture 160 is detachably coupled to a distal end of the imaging structure 31. In one aspect, the suture 160 comprises a four-pronged claw having a cavity 162 through a center of the claw. The cavity 162 is configured to receive and detachably couple to a distal end of the imaging structure 31. In one embodiment, the cavity 162 has a female threaded configuration adapted to receive and secure a male threaded member corresponding to the distal end of the imaging structure 31. However, any suitable connection means is contemplated for use herein. Additionally, while a four-pronged claw is illustrated herein, more or less prongs (e.g., 2 to 10) may be used as suits a particular application. Additionally, the cavity 161 disposed within the claw may be through the center, as described above, or it may be disposed in another portion of the suture 160 as suits a particular application.

In one embodiment of the present invention, the prongs of the suture 160 may be biased in an opened position and restrained in a closed position within outer catheter 165. The suture 160 may be biased by a restraining member (e.g., cord or binding) or it may be restrained by the walls of the outer catheter 165. Once the suturing device 150 has been advanced to a desired location within the patient, the suture 160 may be positioned outside of the outer catheter 165 and opened to its biased position. As has been discussed herein, the suture 160 may comprise a shape memory material which assumes a predetermined shape based on specific temperature regimes. In another aspect, the suture 160 is biased such that the prongs are perpendicular to a longitudinal axis of the outer catheter 165. In this manner, the distal end of the imaging structure 31 may be positioned near the distal end of the outer catheter 165 thereby maximizing image clarity and by default the ability of the medical practitioner to more accurately advance the outer catheter 165 to a desired location within the patient.

Figure 17A:
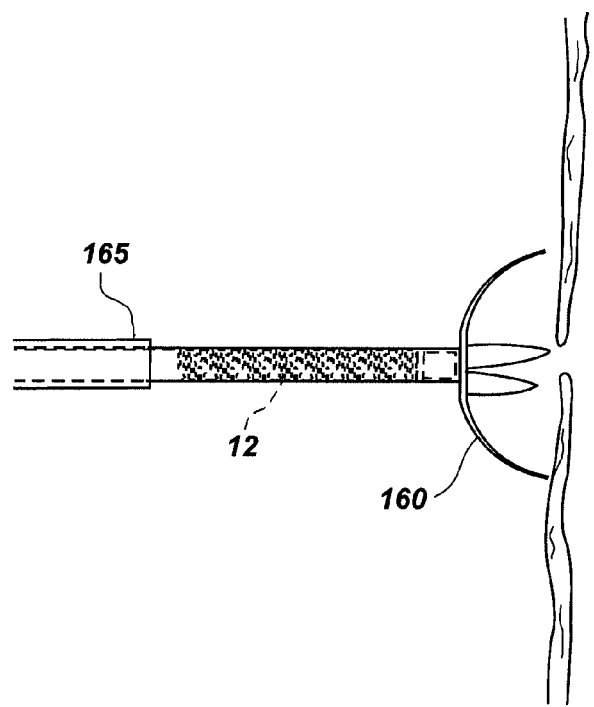
FIG. 17A is a side view of a suture device according to one embodiment of the present invention.
Figure 17B:
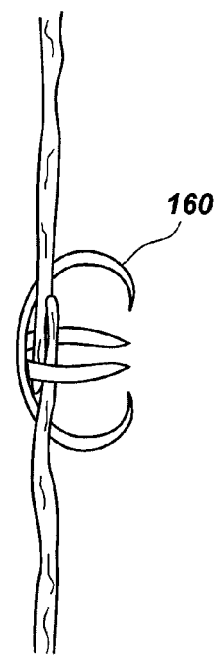
FIG. 17B is a side view of an emplaced suture according to one embodiment of the present invention.

With specific reference to FIGS. 17A and 17B, the suture 160 may be advanced to a desired location within a patient that requires closing (e.g., a patent foramen ovale). While suture 160 is in an open configuration, the suture may be advanced such that the distal ends of the suture 160 puncture, or are placed against, the target tissue. In an aspect where the suture 160 comprises a shape memory material, an electrical current may be applied to the suture 160 causing the suture to assume a closed configuration. In this manner, the suture 160 may be placed in a target tissue while viewing the placement through or substantially proximate to the suture 160.

In another embodiment, the suture may be shaped to approximate the shape of a helix or coil having an imaging structure disposed in the center of the helix and near a proximal end of the helix. In this manner, the helix suture may be advanced and "threaded" or placed into the tissues of the patient. As with the other sutures, the imaging structure allows the medical practitioner to view through the suture itself while placing the suture within the patient. The particular shapes and configurations of sutures referenced herein are not meant to limit the present invention in any way. Rather, any suture employing an imaging structure which is coupled to the suture is contemplated for use herein.

Referring now to FIGS. 4-9 and FIG. 16, a method of placing suture 81 within a patient is disclosed comprising providing a suture 81 disposed on a distal end of a catheter 12, wherein the suture 81 comprises a shape memory material having at least one lumen 30 disposed therein and an imaging structure 31 disposed within the at least one lumen of the suture 81. The imaging structure 31 comprises a SSID 55 optically coupled to a lens system 50. The method further comprises advancing a distal end of the catheter 12 into a portion of a patient and viewing a portion of the interior of the patient with the imaging structure 31. The method further comprises emplacing the suture 81 within a portion of the patient. Emplacement of the suture may be effectuated in numerous ways. For example, in one aspect of the invention, suture 81 further comprises a conductive element detachably coupled to the suture 81. The method further comprises the step of conducting electrical energy to the suture 81 through the conductive element to deform the suture 81 into a predetermined configuration (e.g., a loop shape). The imaging structure 31 may thereafter be withdrawn from the suture 81 and reused or discarded leaving the suture 81 within the patient.

In one aspect of the invention, the method further comprises viewing the target tissue through the distal end of the suture 81 as the target tissue is penetrated by the suture 81. In this manner, a medical practitioner may view the target tissue through, for example, the distal end of the suture 81 as it pierces the target tissue and closes the area which requires suturing. Advantageously, the method allows the practitioner to minimize improper placement of sutures within a patient.

Figure 10:
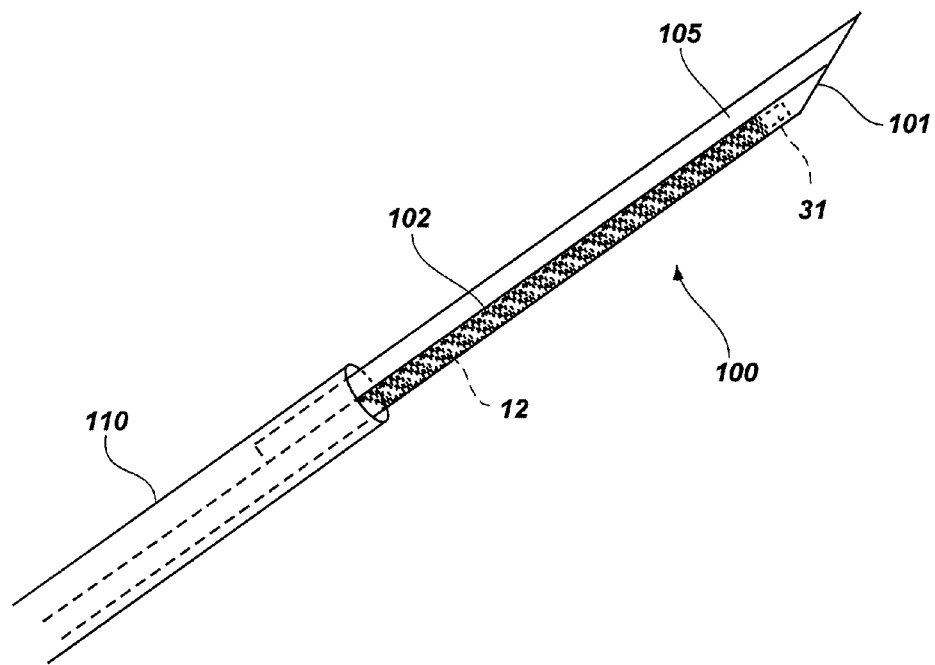
FIG. 10 is a side-view of a micro-camera guided suturing device according to one embodiment of the present invention.
Figure 11:
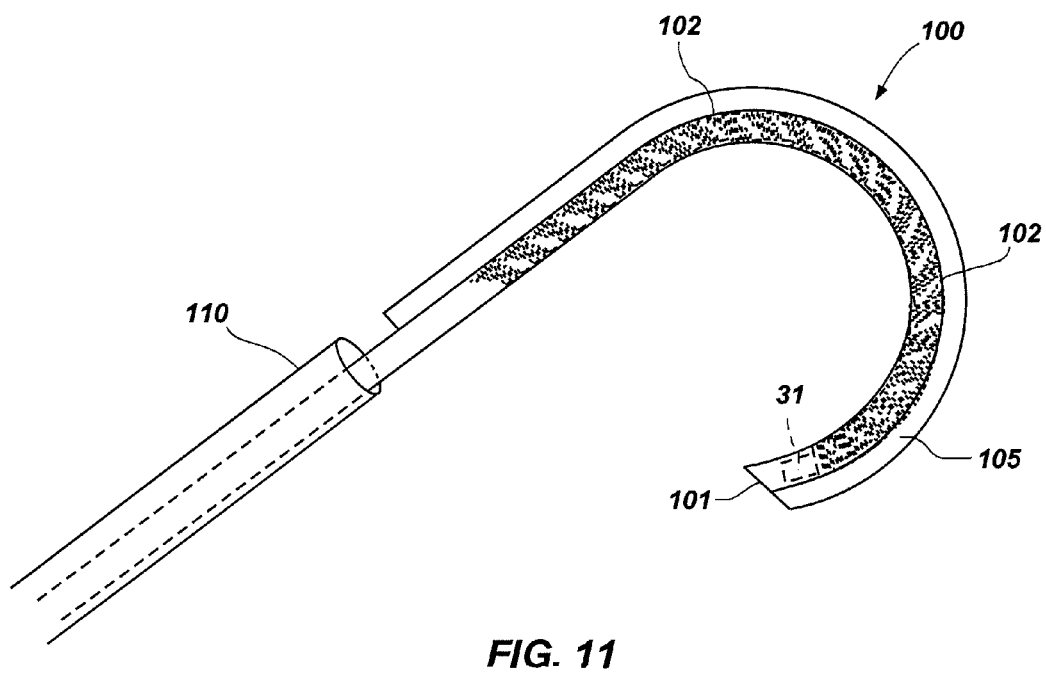
FIG. 11 is a side-view of a micro-camera guided suturing device according to one embodiment of the present invention.
Figure 12:
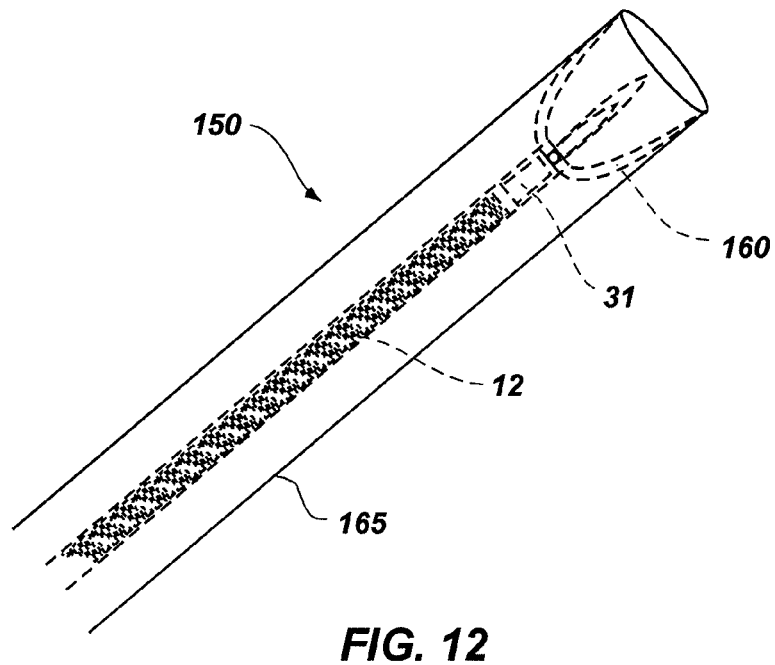
FIG. 12 is a side-view of a micro-camera guided suturing device according to one embodiment of the present invention.
Figure 13:
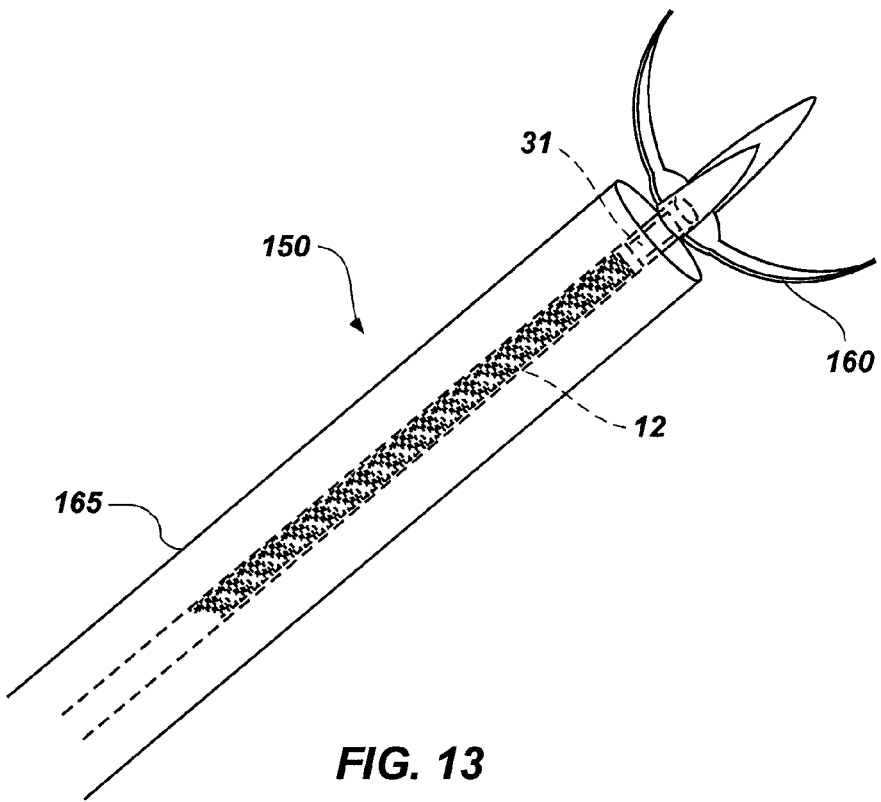
FIG. 13 is a side-view of a micro-camera guided suturing device according to one embodiment of the present invention.
Figure 14:
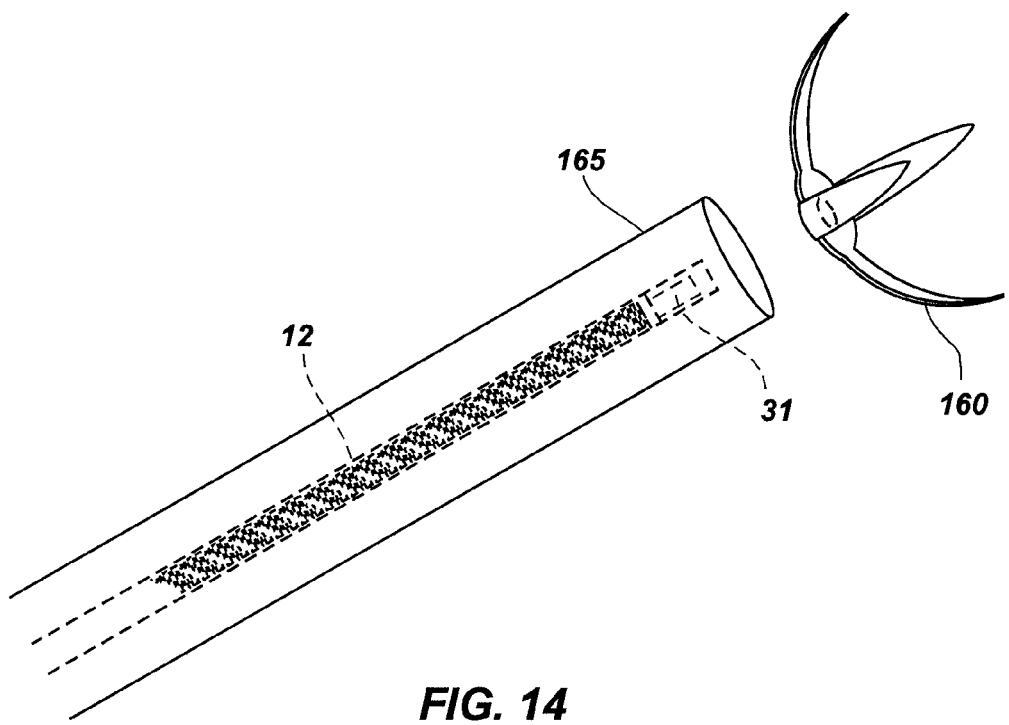
FIG. 14 is a side-view of a micro-camera guided suturing device according to one embodiment of the present invention.
Figure 15:
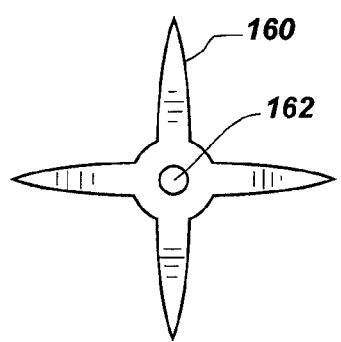
FIG. 15 is a front-view of a suture device according to one embodiment of the present invention.

With reference now to FIGS. 4, 10, and 11 according to an additional embodiment of the present invention, a method of placing suture 105 within a patient is disclosed comprising providing a suture 105 disposed on a catheter 12, wherein the suture 105 comprises a shape memory material and an imaging structure 31 detachably coupled to the suture. The imaging structure 31 comprises a SSID 55 optically coupled to a lens system 50. The method further comprises advancing a distal end of the catheter 12 into a portion of a patient, viewing a portion of the interior of the patient with the imaging structure 31, and emplacing the suture 105 within a portion of the patient while viewing emplacement of the suture 105 with the imaging structure 31.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A micro-camera guided suturing device, comprising:
   a suture comprising an elongate suture body and having at least one lumen terminally disposed therein, wherein the suture functions to join at least two pieces of tissue together and remain in the tissue while the tissues grow together; and
   an imaging structure disposed within the at least one lumen of the suture, the imaging structure comprising a SSID optically coupled to a lens system and configured to image tissue being penetrated by the suture body.

2. The micro-camera guided suturing device of claim 1, further comprising a conductive element detachably coupled to the suture.

3. The micro-camera guided suturing device of claim 2, wherein the conductive element is adapted to heat the suture.

4. The micro-camera guided suturing device of claim 1, wherein the suture comprises a shape memory material.

5. The micro-camera guided suturing device of claim 4 wherein the shape memory material consists of copper-zinc-aluminum-nickel, copper-aluminum-nickel, or nickel-titanium alloys.

6. The micro-camera guided suturing device of claim 4, wherein the shape memory material comprises a shape memory polymer.

7. The micro-camera guided suturing device of claim 6, wherein the shape memory polymer is bioabsorbable.

8. The micro-camera guided suturing device of claim 1, wherein a distal end of the lens system is disposed near a distal end of the suture.

9. The micro-camera guided suturing device of claim 1, wherein the at least one lumen extends longitudinally through approximately the entire suture.

10. The micro-camera guided suturing device of claim 1, wherein the at least one lumen extends longitudinally through a portion of the suture.

11. The micro-camera guided suturing device of claim 1, wherein the image plane of the imaging structure is approximately collinear with a distal end of the suture.

12. The micro-camera guided suturing device of claim 1, comprising at least two imaging structures disposed at the distal end of the suturing device.

13. The micro-camera guided suturing device of claim 1, further comprising an umbilical housing at least one tool selected from the group comprising light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators.

14. A micro-camera guided suturing device comprising:
an elongate tubular member configured for placement within a patient;
a suture comprising an elongate suture body and having at least one lumen terminally disposed within the elongate suture body, wherein the suture functions to join at least two pieces of tissue together and remain in the tissue while the tissues grow together;
an imaging structure disposed within the at least one lumen of the suture, the imaging structure comprising a SSID optically coupled to a lens system and configured to image tissue being penetrated by the suture body.

15. A method of placing a suture within a patient, comprising:
providing a suture disposed within a catheter, the suture comprising a shape memory material having at least one lumen disposed therein and an imaging structure disposed within the at least one lumen of the suture, the imaging structure comprising a SSID optically coupled to a lens system, wherein the suture functions to join at least two pieces of tissue together and remain in the tissue while the tissues grow together;
advancing a distal end of the catheter into a portion of a patient;
viewing a portion of the interior of the patient with the imaging structure; and
emplacing the suture within a portion of the patient and leaving the suture within the patient while the tissues grow together.

16. The method of claim 15, wherein the suture further comprises a conductive element detachably coupled to the suture.

17. The method of claim 16, further comprising the step of conducting electrical energy to the suture through the conductive element to heat the suture.

18. The method of claim 17, further comprising the step of removing the imaging structure from the suture.

19. A micro-camera guided suturing device, comprising:
a steerable micro-catheter having;
a deformable suture disposed within the micro-catheter, comprising an elongate suture body having at least one lumen terminally disposed therein, wherein the suture functions to join at least two pieces of tissue together and remain in the tissue while the tissues grow together; and
an imaging structure disposed within the at least one lumen of the suture, the imaging structure comprising a SSID optically coupled to a lens system and configured to image tissue being penetrated by the suture body.

* * * * *